United States Patent [19]

Ohnishi et al.

[11] 4,122,119

[45] Oct. 24, 1978

[54] PROCESS FOR THE PRODUCTION OF UNSATURATED KETONES

[75] Inventors: Takashi Ohnishi; Yoshiji Fujita; Fumio Wada; Takashi Nishida, all of Kurashiki; Yoshiaki Omura, Mitsu; Fumio Mori, Kurashiki; Takeo Hosogai, Kurashiki; Sukeji Aihara, Kurashiki, all of Japan

[73] Assignee: Kuraray Co., Ltd., Kurashiki, Japan

[21] Appl. No.: 767,801

[22] Filed: Feb. 11, 1977

[30] Foreign Application Priority Data

Feb. 12, 1976 [JP] Japan ............................ 51/15045
Jun. 23, 1976 [JP] Japan ............................ 51/75311
Nov. 8, 1976 [JP] Japan ............................ 51/134300
Nov. 12, 1976 [JP] Japan ............................ 51/136712

[51] Int. Cl.$^2$ .................... C07C 45/00; C07C 49/61
[52] U.S. Cl. ........................ 260/586 C; 260/593 R; 252/522
[58] Field of Search ................ 260/586 C, 593 R

[56] References Cited

U.S. PATENT DOCUMENTS

| | | | |
|---|---|---|---|
| 3,480,677 | 11/1969 | Meuly et al. .................... | 260/586 C |
| 3,668,255 | 6/1972 | Meuly et al. .................... | 260/593 R |
| 3,816,535 | 6/1974 | Hug-Inderbitgin et al. ..... | 260/593 R |
| 3,886,215 | 5/1975 | Desimone et al. ............... | 260/586 C |
| 3,919,250 | 11/1975 | Pauling .............................. | 260/593 R |
| 3,962,311 | 6/1976 | Loeliger ............................ | 260/586 C |
| 3,976,700 | 8/1976 | Desimone ......................... | 260/593 R |

OTHER PUBLICATIONS

Swaminathan et al., Chem. Reviews, vol. 71, No. 5, pp. 429-438 (1971).

*Primary Examiner*—James O. Thomas, Jr.
*Assistant Examiner*—James H. Reamer
*Attorney, Agent, or Firm*—Bacon & Thomas

[57] ABSTRACT

There is disclosed a process for preparing unsaturated ketones especially terpenoid ketones, by subjecting a substituted propargyl alcohol of formula (II)

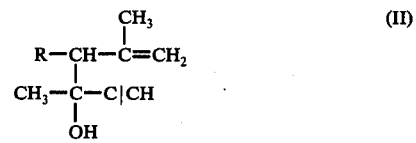

wherein R is a group containing 1 or 2 substituted or unsubstituted alkyl- or alkylene units containing 4 carbon atoms each to a thermal treatment sufficient to rearrange its structure in order to obtain structurally isomeric unsaturated ketones of formula I

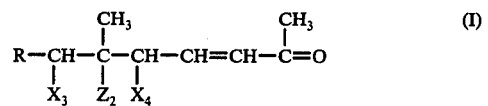

wherein one of the substituents $X_3$ and $X_4$ is hydrogen and the other and $Z_2$ together form a bond. The process can be effected in the presence of an isomerization catalyst, which leads to high percentage of $\alpha.\beta,\gamma.\delta$-unsaturated ketones. The ketones of formula I are useful as perfumes and as intermediates for the production of terpenoid compounds.

28 Claims, No Drawings

PROCESS FOR THE PRODUCTION OF UNSATURATED KETONES

BACKGROUND OF THE INVENTION

This invention relates to a process for producing unsaturated ketones especially unsaturated terpenoid ketones from correspondingly substituted propargyl alcohols.

The rearrangement reaction of a propargyl alcohol to an unsaturated ketone, which is a structural isomer thereof, under the influence of heat is generally known as "Oxy-Cope rearrangement". However, the particular, substituted propargyl alcohols which are used in the present invention have not been subjected to an Oxy-Cope rearrangement, nor is it known that a ketone having a terpenoid structure can be produced by this reaction. Briefly, the prior art relevant to a Oxy-Cope rearrangement reaction will be reviewed. "Oxy-Cope rearrangement" is a term which was coined by J. A. Berson et al who studied this reaction with cyclic compounds (J. Am. Chem. Soc. 86, 5017 and 5019 (1964)). Later, A. Viola et al studied the reaction of acyclic compounds in gaseous phase (J. Am. Chem. Soc. 87, 1150 (1965)). Thereafter, a number of workers did theoretical and applied researches on this reaction. However, as far as propargyl alcohols and its uses are concerned, only A. Viola et al (J.Am.Chem.Soc. 92, 2404 (1970)) are known to have used this reaction. They obtained the unsaturated ketone

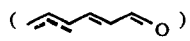

by heating 5-hexen-1-yn-3-ol

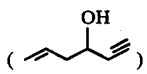

in a gaseous phase at 350° to 390° C.

Typical conventional processes for the production of terpenoid compounds involve a multiple-step procedure comprising the Carroll rearrangement method using diketene which serves as a $C_3$ element for chain extending or the Claisen rearrangement method using isopropenyl ether. For example, the steps which are needed for the production of pseudoionone starting with methyl heptenone may be illustrated as follows [See, e.g., U.S. Pat. No. 2,861,109, British Pat. No. 948,752, W. Kimel et al, J. Org. Chem. 23, 153 (1958) and R. Marbet et al, Angew, Chem., 72, 869 (1960)]

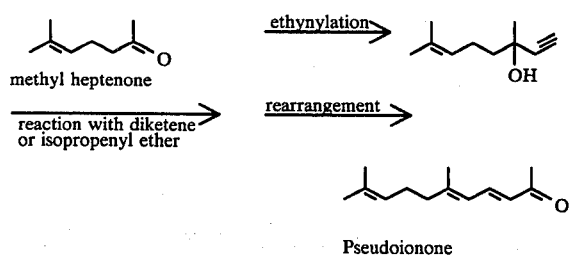

The chain extenders, diketene and isopropenyl ether, are comparatively expensive and such a step of including a chain extending reaction cannot be avoided.

SUMMARY OF THE INVENTION

It is an object of the present invention to provide a process for unsaturated ketones, especially unsaturated terpenoid ketones, which avoids the before mentioned disadvantages and the use of expensive chain extending compounds such as diketene or isopropenyl ether.

It is a further object of the present invention to provide such a process which allows the production of such ketones in an economical way using less reaction steps than those of conventional processes.

It is a further object of the present invention to provide a process which allows the production of such ketones from easily obtainable and inexpensive starting materials.

It is a further object of the present invention to provide a process which allows to selectively prepare $\alpha,\beta,\gamma,\delta$-unsaturated ketones.

In order to accomplish the foregoing objects according to the present invention there is provided a process for preparing unsaturated ketones which comprises the step of subjecting a substituted propargyl alcohol of formula (II).

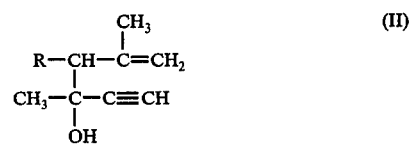

wherein R represents a

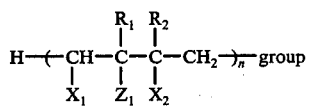

wherein one of the substituents $X_1$ and $X_2$ is hydrogen and the other and $Z_1$ together form a bond or both $X_1$ and $X_2$ are hydrogen and $Z_1$ represents hydrogen, hydroxyl or lower alkoxy, $R_1$ represents a hydrogen or lower alkyl, $R_2$ represents hydrogen or lower alkyl and n represents 1 or 2 whereby if n is 2 the substituents $X_1$, $X_2$, $Z_1$, $R_1$ and $R_2$ within the 2 units are alike or different from each other to a thermal treatment sufficient to rearrange its structure in order to obtain a rearranged ketone product containing structurally isomeric unsaturated ketones of formula (I)

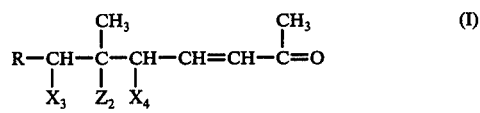

wherein one of the substituents $X_3$ and $X_4$ is hydrogen and the other and $Z_2$ together form a bond and R is as defined above.

The unsaturated ketones of formula (I) are useful not only as perfumes, per se, but also as intermediates for the production of other perfumery compounds such as ionone and irone, pharmaceuticals, agricultural chemicals, various coloring materials and so forth.

If in the group H etc. As preferred examples of R, the following are cited.

| Nomenclature of group R | Chemical formula |
|---|---|
| n-Butyl | $CH_3CH_2CH_2CH_2-$ |
| Isoamyl | $CH_3-\overset{\underset{\mid}{CH_3}}{CH}-CH_2-CH_2-$ |
| Prenyl | $CH_3-\overset{\underset{\mid}{CH_3}}{C}=CH-CH_2-$ |
| 3-Methyl-3-butenyl | $CH_2=\overset{\underset{\mid}{CH_3}}{C}-CH_2-CH_2-$ |
| 2,3-Dimethyl-3-hydroxy butyl | $CH_3-\overset{\underset{\mid}{OH}}{\underset{\mid}{C}}-\overset{\underset{\mid}{CH_3}}{CH}-CH_2-$ |
| 3-Methyl-2-pentyl | $\overset{\underset{\mid}{C_2H_5}}{CH_3-C=CH-CH_2-}$ (with $CH_3$ substituent) |
| 2,3-Dimethyl-2-butenyl | $CH_3-\overset{\underset{\mid}{CH_3}}{C}=\overset{\underset{\mid}{CH_3}}{C}-CH_2-$ |
| 2,3-Dimethyl-3-butenyl | $CH_2=\overset{\underset{\mid}{CH_3}}{C}-\overset{\underset{\mid}{CH_3}}{CH}-CH_2-$ |
| 2,3-Dimethyl-2-pentenyl | $CH_3=\overset{\underset{\mid}{C_2H_5}}{C}=\overset{\underset{\mid}{CH_3}}{C}-CH_2-$ |
| 2-Ethyl-3-methyl-2-butenyl | $CH_3-\overset{\underset{\mid}{CH_3}}{C}=\overset{\underset{\mid}{C_2H_5}}{C}-CH_2-$ |
| 2,3-Dimethyl-3-methoxybutyl | $CH_3-\overset{\underset{\mid}{OCH_3}}{\underset{\mid}{C}}(CH_3)-\overset{\underset{\mid}{CH_3}}{CH}-CH_2-$ |
| 3,7-Dimethyloctyl | $CH_3-\overset{\underset{\mid}{CH_3}}{CH}-(CH_2)_3-\overset{\underset{\mid}{CH_3}}{CH}-CH_2CH_2-$ |
| 3,7-Dimethyl-2,6-octadienyl | $CH_3-\overset{\underset{\mid}{CH_3}}{C}=CH-(CH_2)_2-\overset{\underset{\mid}{CH_3}}{C}=CH-CH_2-$ |
| 3,7-Dimethyl-2,7-octadienyl | $CH_2=\overset{\underset{\mid}{CH_3}}{C}-CH_2CH_2CH_2-\overset{\underset{\mid}{CH_3}}{C}=CH-CH_2-$ |
| 3,7-Dimethyl-6-octenyl | $CH_3-\overset{\underset{\mid}{CH_3}}{C}=CH-(CH_2)_2-\overset{\underset{\mid}{CH_3}}{CH}-CH_2-CH_2-$ |
| 3,7-Dimethyl-2-octenyl | $CH_3-\overset{\underset{\mid}{CH_3}}{CH}-(CH_2)_3-\overset{\underset{\mid}{CH_3}}{C}=CH-CH_2-$ |
| 7-Methyl-3-ethyl-2,6-nonadienyl | $CH_3-\overset{\underset{\mid}{C_2H_5}}{C}=CH-(CH_2)_2-\overset{\underset{\mid}{C_2H_5}}{C}=CH-CH_2-$ |
| 3,7-Dimethyl-7-hydroxy octyl | $CH_3-\overset{\underset{\mid}{OH}}{\underset{\mid}{C}}(CH_3)-(CH_2)_3-\overset{\underset{\mid}{CH_3}}{CH}-CH_2CH_2-$ |
| 3,7-Dimethyl-7-methoxy octyl | $CH_3-\overset{\underset{\mid}{OCH_3}}{\underset{\mid}{C}}(CH_3)-(CH_2)_3-\overset{\underset{\mid}{CH_3}}{CH}-CH_2CH_2-$ |

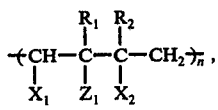

$Z_1$ is a lower alkoxy group, said alkoxy group is preferably methoxy, ethoxy, propoxy or butoxy. If $R_1$ and $R_2$ are both lower alkyl groups, these alkyl groups preferably contain 1 to 5 carbon atoms, such as methyl, ethyl, n-propyl, isopropyl, n-butyl, t-butyl, n-amyl, isoamyl, The substituted propargyl alcohols which exhibit the particular structure which is needed to form the compounds of formula (I) according to the present invention are prepared using mesityl oxide (i.e., 4-methyl-3-penten-2-one;

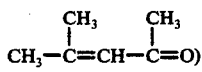

and/or isomesityl oxide (i.e., 4-methyl-4-penten-2-one;

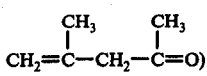

as starting materials.

The substituted propargyl alcohols of formula (II) are prepared by a process which is shown in the following reaction scheme below and which comprises the steps of (a) reacting a halide of the formula R-halo, wherein R is as defined above and halo represents a halogen atom with mesityl oxide and/or isomesityl oxide to obtain a reaction product which contains an α,β-unsaturated ketone of the formula (IV) below and/or a β,γ-unsaturated ketone of the formula (III) below, and (b) ethynylating said ketone or ketones.

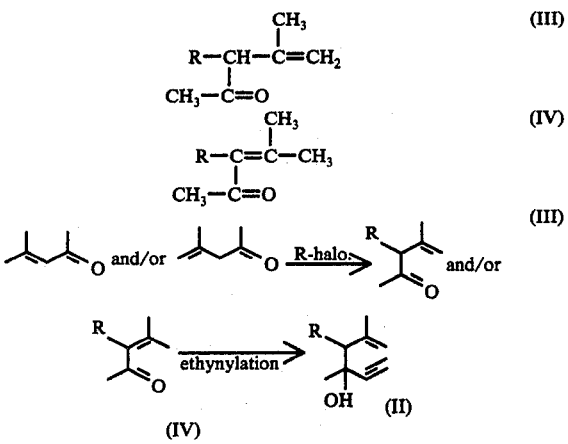

The substituted propargyl alcohols of formula (II) and their preparation are described in the invention, copending U.S. patent application Ser. No. 746,738, filed Dec. 2, 1976, the disclosure of which is hereby incorporated by reference.

Preferably an isomerization of an α,β-unsaturated ketone of formula (IV) within the above-mentioned reaction product into the β,γ-unsaturated ketone of formula (III) is effected prior to or simultaneously with the ethynylation.

The ethynylation of the ketones is performed by reacting them with acetylene in the presence of a catalytic amount of a strongly basic alkali metal compound and a polar organic solvent and/or liquid ammonia. When this ethynylation is performed under an elevated acetylene pressure, an isomerization of an α,β-unsaturated ketone into the corresponding β,γ-unsaturated ketone is achieved simultaneously.

The thermal treatment of the propargyl alcohols of formula (II) is effected at elevated temperatures in a liquid or a gaseous phase and usually yields a mixture of α,β,γ,δ-unsaturated and α,β,δ,ε-unsaturated ketones. Preferably, the reaction is effected in the presence of a liquid polar organic compound. In order to obtain mainly α,β,γ,δ-unsaturated ketones the reaction preferably is effected in the presence of an isomerization catalyst. According to another embodiment of the invention, the rearranged product is subject to an independent isomerization step after the rearrangement reaction.

Further objects, features and advantages of the present invention will become apparent from the detailed description of the invention and its preferred embodiments which follow.

(1) Production of the α,β-unsaturated ketone and the β,γ-unsaturated ketone

The production of the α,β-unsaturated ketone and β,γ-unsaturated ketone which are employed in the production of the substituted propargyl alcohols does not constitute an essential part of the invention, the ketones being prepared by procedures known, per se.

For reference's sake, the production processes for these ketones will be described below.

Mesityl oxide and isomesityl oxide have been commercially produced by the dehydration of diacetone alcohol which is a dimer of acetone. Depending upon the production conditions, the formed 4-methylpentene-2-one comprises about 5 to 20 percent of 4-methyl-4-pentene-2-one (isomesityl oxide) and the rest is 4-methyl-3-pentene-2-one (mesityl oxide).

Mesityl oxide and isomesityl oxide can be separated from each other by distillation and each of them may be used in the reaction with the organic halide R-halo. However, it is more practical to subject the mixture of mesityl oxide and isomesityl oxide to the contemplated reaction. The production of substituted ketones by reacting ketones with organic halides is a generally known method. It is also known that, preferably the reaction is conducted in the presence of a catalyst, such as an amine compound, tertiary ammonium salt or phosphonium compound and/or an alkaline condensing agent such as sodium hydroxide or potassium hydroxide (see, for example, British Pat. No. 851,658 and No. 1,059,839 and U.S. Pat. No. 3,668,255). According to the present invention, the reaction of the organic halide with mesityl oxide and/or isomesityl oxide is conducted in a manner conventional per se. Also, when pure mesityl or isomesityl oxide are employed, the reaction product generally contains both a β,γ-unsaturated ketone of formula (III) and an α,β-unsaturated ketone of formula (IV). In the above reaction, the alkaline condensing agent is used in an amount of about 1 to about 10 mole equivalents, preferably an amount of about 1.5 to 4 moles, per mole of the organic halide (R-halo). The alkaline condensing agent is added to the reaction system, either as it is or in the form of an aqueous solution containing about 40 to 65 weight percent of said agent. The catalyst may be a primary amine, secondary amine or tertiary amine, a salt of such an amine, a quaternary ammonium salt or a phosphonium salt, preferred species including tetrabutylammonium chloride, trimethylbenzylammonium chloride, trimethyllaurylammonium chloride, trimethyl cetylammonium chloride, trimethylstearylammonium chloride, trimethylstearylammonium bromide, dimethyldicyclohexylphosphonium chloride, methyltricyclohexylphosphonium chloride, ethyltricyclohexylphosphonium chloride and ethyltricyclohexylphosphonium bromide. The preferred amount of said catalyst is generally in the range of about 0.001 to 20 mole percent and, for still better results, about 0.005 to 2.0 mole percent based on the organic halide. The reaction temperature may be chosen within the range of 0° to 100° C., although the range of about 20° to 70° C. is particularly desirable. Under the conditions described above, the reaction is completed in about 1 to 30 hours. Where it is desired to obtain a higher ratio of β,γ-unsaturated ketone (III) to α,β-unsaturated ketone (IV) in connection with the above reaction, it is advisable to terminate the reaction when the conversion of the organic halide has reached about 70 to 80 percent. This higher ratio of β,γ-ketone to α,β-ketone is preferred since the α,β-unsaturated ketone of formula (IV) does not easily react in an ethynylation reaction to produce the corresponding propargyl alcohol of the following formula (II′).

(II′)

(wherein R is as defined hereinbefore). However, it is worth mentioning that even when mesityl oxide alone is used in said reaction with an organic halide, an appreciable amount of β,γ-unsaturated ketone is produced as mentioned hereinbefoe. Because of the different boiling points of the α,β-unsaturated ketone and β,γ-unsaturated ketone, the α,β-unsaturated ketone may be separated, if necessary, by distillation from the reaction mixture but, so far as the production of the propargyl alcohol of this invention is concerned, it is normally not necessary to separate the two ketones (III and IV) from each other.

In order to obtain a substituted propargyl alcohol of formula (II) from the α,β-unsaturated ketone, an isomerization of said ketone to the β,γ-unsaturated ketone of formula (III) has to take place. This isomerization may be performed in an independent reaction prior to the ethynylation reaction by heating the ketone in the presence of an acid catalyst. The isomerization may be effected with the isolated α,β-unsaturated ketone or a mixture of the ketones which contain an amount of α,β-unsaturated ketone which is higher than the amount which corresponds to the thermal equilibrium between the two unsaturated ketones. Because the β,γ-unsaturated ketone is lower-boiling than the α,β-unsaturated ketone, a mixture of the two ketones may be subjected to the distillation under conditions which are suited for the isomerization of a α,β-unsaturated ketone, whereby the β,γ-unsaturated ketone alone may be continuously recovered from the mixture as the distillate. In order to provide for an easy separation and recovery of the β,γ-unsaturated ketone by distillation after or during the isomerization step, preferably an acid which exhibits a higher boiling point than the β,γ-unsaturated ketone is used as an acid catalyst for the isomerization. Examples of such acids are aliphatic or aromatic sulfonic acids such as benzenesulfonic acid, p-toluenesulfonic acid, laurysulfonic acid, etc.; monocyclic, aromatic or alicyclic mono-, di- or polycarboxylic acids which may contain a hetero-atom, such as p-toluic acid, 4-nitro-m-toluic acid, 4-hydroxybenzoic acid, vanillic acid, 4-nitroisophthalic acid, cyclohexanecarboxylic acid, etc.; saturated or unsaturated aliphatic or heteroaliphatic mono-, di- or polycarboxylic acids which may have a hydroxyl group or a phenyl substituent, such as adipic acid, 1,2-hydroxystearic acid, benzylic acid, p-nitrocinnamic acid, diglycolic acid, etc.; aliphatic or aromatic amino acids such as indolebutyric acid, 1,2-diaminocyclohexanetetraacetic acid, etc.; and inorganic acids such as metaphosphoric acid, phenylphosphinic acid and the like. The amount of said acid catalyst depends on the type of catalyst. For sulfonic acids, for instance, an amount of about 0.01 to about 0.1 mole percent relative to the α,β-unsaturated ketone is advisable and for other acids, amounts of about 0.1 to about 20 mole percent and, preferably about 4 to about 8 mole percent relative to the amount of the α,β-unsaturated ketone. The reaction temperature is preferably in the range of about 80° to 200° C.

Another method for isomerization of the α,β-unsaturated ketone is such that, in an independent reaction, prior to the ethynylation reaction, the ketone is contacted with a base. The α,β-unsaturated ketone may be used alone or in admixture with the β,γ-unsaturated ketone. Exemplary of the aforementioned bases, the following are cited: alkali metal hydroxides (e.g., sodium hydroxide, lithium hydroxide and potassium hydroxide), alkaline earth metal hydroxides (e.g., calcium hydroxide and barium hydroxide), weak acid salts of alkali metals (e.g., sodium carbonate, potassium carbonate, sodium acetate and potassium acetate), weak acid salts of alkaline earth metals (e.g., calcium carbonate and magnesium carbonate), alkali metal amides (e.g., lithium amide, sodium amide and potassium amide), alkali metal alcoholates (e.g., sodium methoxide, sodium ethoxide, sodium tert.-butoxide and potassium tert.-butoxide) and organic nitrogen-containing bases including tertiary amines, secondary amines and cyclic amines (e.g., triethylamine, monoethanolamine, diethanolamine, triethanolamine, 1,5-diazabicyclo-[3.4.0]nonene-5, 1,5-diazabicyclo-[5.4.0]undecene-5 (abbreviated name: DBU), 2-dimethylamino-1-pyrroline, 1,4-diazabicyclo[2.2.2]octane (abbreviated name: DABCO), 5-methyl-1-azabicyclo-[3.3.0]octane and hexamethylenetetramine). If these bases are solids, preferably solutions are used which contain these bases dissolved in a suitable solvent such as liquid ammonia, N-methylpyrrolidone, dimethylformamide, dimethylsulfoxide, methanol or ethanol. If such bases are water-solution, aqueous solutions thereof may be used. Among alkali- and alkaline earth metal-containing bases, alkali metal hydroxides are particularly suitable with respect to the rate of isomerization and preferably are used as a 20 to 60 weight percent solution in water and in combination with a quaternary ammonium salt or phosphonium salt, i.e., the catalysts which have been previously mentioned in connection with the reaction of an organic halide (R-halo) with mesityl oxide and/or isomesityl oxide. The catalyst may be employed in the range of 0.001 to 10 mole percent based on the alkali metal hydroxide employed, although the range of 0.1 to 3 mole percent is particularly advisable. The base may be used in amounts of about 1 to about 400 weight percent relative to the weight of the α,β-unsaturated ketone in order to provide for good results as far as such factors as reaction velocity, economics and reaction temperatures are concerned. The preferred reaction temperature is somewhere between 50° and 200° C. for organic nitrogen-containing bases, and between −10° and +100° C. for other bases. The bases which are most preferred for the process according to the present invention are organic nitrogen-containing strong bases such as DBU and DABCO and aqueous solutions of sodium hydroxide or potassium hydroxide. After the isomerization reaction, the β,γ-unsaturated ketone may be separated from the reaction mixture by distillation. Alternatively, a base (e.g., DBU) which has a higher boiling point than the α,β- and β,γ-unsaturated ketones and which provides for a high rate of isomerization may be used and the β,γ-unsaturated ketone may be continuously distilled off from the mixture of the ketones during the isomerization reaction.

(2) Production of the substituted propargyl alcohol

It has been known before that compounds which have a propargyl alcohol structure may be produced by ethynylation of ketones. In this connection reference is made to U.S. Pat. Nos. 3,082,260 and 3,496,240 and U.S. published patent application Ser. No. B 460,846 and "Acetylenic Compounds, Preparation and Substitution Reactions" by Thomas F. Rutledge (Reinhold Book Corp., 1968).

For the preparation of a substituted propargyl alcohol of formula (II) which is used in the present invention, the ethynylation of a β,γ-unsaturated ketone of formula (III) or a mixture of said ketone (III) and an α,β-unsaturated ketone of formula (IV) may be performed by a procedure known per se. As preferred examples of such ethynylation procedures the following are mentioned:

(a) The reaction of the ketones with acetylene in the presence of a catalytic amount of a strongly basic alkali metal compound and in an organic polar solvent such as N,N-dimethylformamide, dimethylsulfoxide, N-methylpyrrolidone, tetrahydrofuran, dimethyl ether, diethyl ether, methyl ethyl ether, anisole or dioxane.

(b) The reaction of the ketones with acetylene in the same manner as described above (a) except that liquid ammonia is employed as a solvent in lieu of an organic polar solvent.

(c) The reaction of the ketones with acetylene in the same manner as described above (a) except that a mixture of liquid ammonia and an organic polar solvent is employed as the solvent.

The aforementioned ethynylation processes require only simple separation techniques and are less expensive than other ethynylation processes which involve the use of a Grignard reagent such as an ethynylmagnesium halide, or an alkali metal- or alkaline earth metal acetylide. As far as the recovery of the solvent and the separation of the product are concerned, the above process (b) is particularly advisable. Strongly basic alkali metal compounds which may be used as a catalyst are sodium and potassium hydroxides; sodium and potassium alkoxides containing 1 to 5 carbon atoms such as sodium methoxide, sodium ethoxide, sodium butoxide, potassium ethoxide, potassium butoxide, etc.; and sodium and potassium amides. Particularly preferred are the potassium compounds. It is possible to add precursors capable of giving rise to such a basic compound to the reaction system so that said compound may be produced in situ. These basic compounds may be dissolved in water, alcohol or another solvent before being added to the reaction system. While there is no particular limitation on the amount of such a basic compound, it is preferable, for the purposes of commercial production, that said base be used in amounts of about 0.1 to about 30 mole percent and, for still better results, of about 1 to about 10 mole percent relative to the unsaturated ketone. Generally, the reaction is conducted by contacting acetylene with a solution of the unsaturated ketone in the solvent in the presence of said alkali metal compound. The amount per volume of the reaction solvent is preferably at least equal to that of the unsaturated ketone, the range of twice to 20 times the volume of the unsaturated ketone is particularly advisable.

From the prior art, for example, U.S. published patent application Ser. No. B 460,846, it might be expected that the ethynylation of a α,β-unsaturated ketone in the present invention would lead to a substituted propargyl alcohol of formula (II'). Unexpectedly, however, it has been found that when said ethynylation reaction is performed under elevated acetylene pressure, the isomerization of the α,β-unsaturated ketone of formula (IV) to the β,γ-unsaturated ketone of formula (III) takes place in situ and, furthermore, the ethynylation of β,γ-unsaturated ketone is promoted simultaneously. Further studies have indicated that this reaction is specific to such α,β-unsaturated ketones which include a hydrocarbon substituent such as the group R hereinbefore mentioned in the position alpha to the carbonyl group. The term 'elevated pressure of acetylene' as used herein means that acetylene is present in the reaction system in an amount exceeding its solubility in the solvent and in excess of the amount that will be consumed in the ethynylation reaction. In terms of the partial pressure of acetylene within the reaction system, such a pressure is preferably corresponding to a pressure of about 1 kg/cm$^2$ guage to about 15 kg/cm$^2$ gauge at 0° C. Therefore, when the ethynylation reaction is carried out under such elevated acetylene pressures may not only be the β,γ-unsaturated ketone or a mixture of β,γ-unsaturated ketone and α,β-unsaturated ketone but also be the α,β-unsaturated ketone alone may be used. This means that it is neither necessary to separate and remove the α,β-unsaturated ketone from the mixture of a α,β-unsaturated ketone and a β,γ-unsaturated ketone which is obtained by the reaction of an organic halide (R-halo.) with mesityl oxide and/or isomesityl oxide, nor is it necessary to subject the ketone to a separate isomerization reaction. The reaction temperature may range from −33° C. to +30° C. and, preferably, from −15° C. to +15° C. The elevated acetylene pressure is effective in promoting the isomerization of the α,β-unsaturated ketone promoting the conversion of an β,γ-unsaturated ketone (III) to a propargyl alcohol (II), and in suppressing the deethynylation reaction of the formed propargyl alcohol to a β,γ-unsaturated ketone of formula (III). In this case, the formation of a propargyl alcohol of formula (II') structurally corresponding to the α,β-unsaturated ketone may be disregarded.

When the ethynylation reaction is carried out in the reaction system under atmospheric pressure while bubbling acetylene through the reaction system (hereinafter referred to as "released system of acetylene"), either only the β,γ-unsaturated ketone or a mixture containing a predominant part of said ketone and a minor part of α,β-unsaturated ketone should be used because in such a system the isomerization of the α,β-unsaturated ketone to the β,γ-unsaturated ketone takes place with difficulty. In any event, the substituted propargyl alcohol of formula (II') is scarcely formed from the α,β-unsaturated ketone.

After the ethynylation reaction, the unreacted β,γ-unsaturated ketone (III) and/or α,β-unsaturated ketone (IV) and/or such ketones that might be contained in the reaction mixture as originating from the isomerization reaction may be recovered by distillation and subjected to the isomerization reaction and/or ethynylation reaction to obtain an additional amount of the propargyl alcohol.

Preferred examples of the propargyl alcohols of formula (II) which can thus be obtained by said ethynylation reaction are those which contain the preferred groups R mentioned hereinbefore. Thus, these alcohols include:

4-Isopropenyl-3-methyl-1-octyn-3-ol,
4-Isopropenyl-3,7-dimethyl-1-octyn-3-ol,
4-Isopropenyl-3,7-dimethyl-1-octyn-6-en-3-ol,
4-Isopropenyl-3,7-dimethyl-1-octyn-7-en-3-ol,
4-Isopropenyl-3,7-dimethyl-1-nonyn-6-en-3-ol,
4-Isopropenyl-3,7,11-trimethyldodeca-1-yn-3-ol,
4-Isopropenyl-3,7,11-trimethyldodeca-1-yn-6,10-dien-3-ol,
4-Isopropenyl-3,7,11-trimethyldodeca-1-yn-10-en-3-ol,
4-Isopropenyl-3,7,11-trimethyldodeca-1-yn-6-en-3-ol,
4-Isopropenyl-3,11-dimethyl-7-ethyltrideca-1-yn-6,10-dien-3-ol,
4-Isopropenyl-3,7,11-trimethyldodeca-1-yn-6,11-dien-3-ol,
4-Isopropenyl-3,7,11-trimethyldodeca-1-yn-3,11-diol,
4-Isopropenyl-3,7,11-trimethyl-11-methoxydodeca-1-yn-3-ol,
4-Isopropenyl,3,6,7-trimethyl-1-octyn-3,7-diol,
4-Isopropenyl-3,6,7-trimethyl-7-methoxy-1-octyn-3-ol,
4-Isopropenyl-3,6,7-trimethyl-1-octyn-6-en-3-ol,
4-Isopropenyl-3,6,7-trimethyl-1-octyn-7-en-3-ol,
4-Isopropenyl-3,6,7-trimethyl-1-nonyn-6-en-3-ol, and
4-Isopropenyl-6-ethyl-3,7-dimethyl-1-octyn-3-ol.

(3) Production of α.β,γ.δ-Unsaturated Ketones and α.β,δ.ε-Unsaturated Ketones

According to the present invention the unsaturated ketones of formula (I) can be produced by a rearrangement reaction which comprises heating a substituted propargyl alcohol of formula (II). The resulting product is normally a mixture of an α.β,γ.δ-unsaturated ketone of formula (I-1):

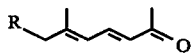   (I-1)

and an α.β,δ.ε-unsaturated ketone of formula (I-2):

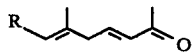   (I-2)

This rearrangement reaction may be carried out in a liquid phase or a gaseous phase. While the reaction temperature may range from 100° to 450° C., with regard to the reaction speed and selectivity, it is preferred to apply a temperature of about 100° to about 250° C., particularly of about 130° to about 230° C., for a liquid phase reaction, or of about 250° to about 400° C. for a gaseous phase reaction, whereby the optimum temperature depends upon the length of the reaction period. The reaction may be conducted in an ambient atmosphere. However, it is generally preferable to carry out the reaction under an inert gaseous atmosphere such as nitrogen or helium in order to preclude occurrence of undesirable side reactions. The reaction pressure is not particularly critical and the reaction normally proceeds satisfactorily at atmospheric pressure. However, in the gaseous phase reaction, as well as in the liquid phase reaction wherein the boiling point at atmospheric pressure of the substituted propargyl alcohol or of the solvent, if any is lower than the reaction temperature, it may be necessary to work under an elevated pressure which is appropriate to the other reaction conditions. Since this very reaction is a thermal reaction, the length of the reaction period is dependent on the temperature which is used. Thus, for example, the reaction period is from about 2 to about 15 hours if the reaction temperature is between about 150° and about 190° C. In the liquid phase reaction, the use of a solvent is not essential, although it is permissible to use a solvent such as an alcohol, e.g., methanol and ethanol, and aromatic hydrocarbons, e.g., benzene, toluene and xylene.

The rearrangement of a substituted propargyl alcohol of formula (II) to a terpenoid ketone of formula (I) by heating in accordance with the present invention, permits the production of the desired terpene compounds with extreme ease and at low cost as compared with conventional production processes for producing terpenoid ketones with the aid of chain extenders. However, the selectivity of the reaction with respect to the intended ketones of formula (I) is not as high as is desirable. More specifically, because the selectivity which can be attained by the above process is only as low as about 50 percent, it is desired to enhance the selectivity in order to render the process more economical.

In this connection, it has been found that the use of a liquid polar organic compound containing a sulfoxide group

an amido group

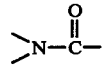

or a phosphoryl group

(hereinafter referred to as "additive") is effective to bring about a significant improvement in the selectivity of the rearrangement reaction in liquid phase. The additives mentioned above may be selected from a broad range of compounds under the proviso that they are stable under the conditions of the rearrangement reaction according to the present invention and do not get directly involved in the reaction and the reaction conditions are such that they remain liquid. Because of their easy availability, preferred additives are, e.g., dimethyl sulfoxide, diethyl sulfoxide, tetramethylene sulfoxide, dimethylformamide, dimethylacetamide, diethylformamide, diethylacetamide, pyrrolidone, N-methylpyrrolidone, N-ethylpyrrolidone, ε-caprolactam, hexamethyl phosphoramide, hexaethyl phosphoramide, trimethyl phosphate and triethyl phosphate.

In practice, an increase in the amount of said additive will tend to improve the selectivity for forming the unsaturated ketones of formula (I). Usually it is practical to use the additive in an amount of not more than 20 times the volume of the substituted propargyl alcohol of formula (II). The effect of the additive is generally observed when it is used in an amount of at least about 0.5 times the volume of said propargyl alcohol. According to the type of additive which is used, the ratio of the formed α.β,γ.δ-unsaturated ketone to the α.β,δ.ε- unsaturated ketone may vary. For example, whereas the ratio of 6,10-dimethyl-3,6,9-undecatrien-2-one to 6,10-dimethyl-3,5,9-undecatrien-2-one is about 9:1 when 4-isopropenyl-3,7-dimethyl-1-octyn-6-en-3-ol is reacted in the presence of N-methylpyrrolidone as the additive (the ratio propargyl alcohol:the additive = 1:3 by vol.) at 165° C. for 4 hours, a larger proportion of the latter ketone is obtained if dimethylsulfoxide is used in lieu of N-methylpyrrolidone.

The hereinbelow mentioned group of unsaturated ketones which can be prepared according to the present invention are considered especially valuable and can be commercially used for many purposes. One of them is a group of unsaturated ketones of the formula (I-a) below, which can be obtained from the substituted propargyl alcohol of the formula (II-a) below, wherein $R_2$ is hydrogen or methyl, and which correpsonds to compounds of formula I, wherein within the above defined group R, one of the substituents $X_1$ and $X_2$ is hydrogen, and the other together with $Z_1$ forms a bond, $R_1$ is methyl, $R_2$ is hydrogen or methyl, and $n$ is 1.

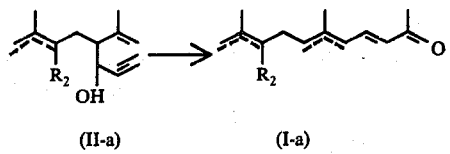

(II-a)  (I-a)

In the above formulas (I-a) and (II-a), the dotted lines each mean that one of the positions indicated thereby is a carbon-to-carbon double bond. Another group of useful unsaturated ketones which are prepared according to this invention comprises the unsaturated ketones of the formula (I-b) below, which are obtainable from the substituted propargyl alcohols of formula (II-b) and which correspond to compounds of formula (I), wherein within the above defined group R, $n$ is 2, $X_1$, $X_2$, $Z_1$, $R_1$ and $R_2$, respectively, are the same in the two units and one of the substituents $X_1$ and $X_2$ is hydrogen, and the other together with $Z_1$ forms a bond, $R_1$ is methyl and $R_2$ is hydrogen.

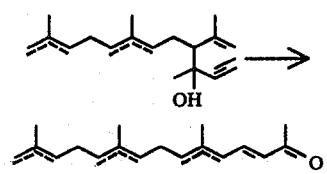

In the formulas, the dotted lines each mean that either one of the positions indicated thereby is a carbon-to-carbon double bond.

The unsaturated ketones which can be obtained according to this invention correspond to the propargyl alcohols which are described hereinbefore, and the following may be mentioned as examples of the unsaturated ketones not subsumed in the above generic formulas, (I-a) and (I-b).

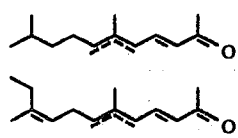

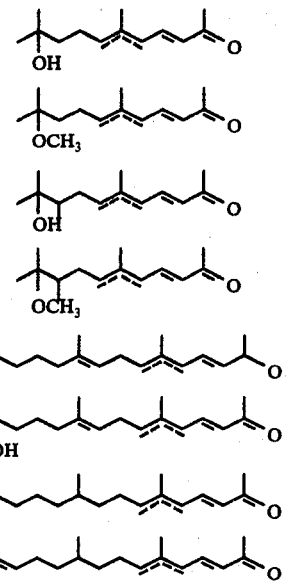

(4) Isomerization of the $\alpha.\beta,\delta.\epsilon$-Unsaturated Ketones

As mentioned hereinbefore, a unsaturated ketone produced according to this invention is a mixture of the $\alpha.\beta,\gamma.\delta$-unsaturated ketone (I-1) and the $\alpha.\beta,\delta.\epsilon$-unsaturated ketone (I-2). While the position of the carbon-to-carbon double bond in said unsaturated ketone is not so critical as far as certain applications are concerned, for other uses, for example, the preparation of ionones or irones through cyclization, the unsaturated ketones containing a double bond in $\gamma.\delta$-position to carbonyl groups as indicated by the formula (I-1) are desired. The unsaturated ketones in which the double bond is situated at the $\gamma.\delta$-position to the carbonyl group satisfy both the formula (I-1) and either one of the formulas (I-a) and (I-b). Therefore, the formulas of such unsaturated ketones may be written as (I-1-a) and (I-1-b), respectively.

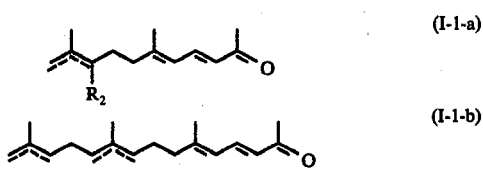

In the above formula (I-1-a), the dotted lines means that a double bond exists at one of the indicated positions and $R_2$ is hydrogen or methyl. In the formula (I-1-b), the dotted lines each means that a double bond exists at one of the positions thereby indicated. The $\alpha.\beta,\delta.\epsilon$-unsaturated ketones corresponding to the $\alpha.\beta,\gamma.\delta$-unsaturated ketones of formulas (I-1-a) and (I-1-b), respectively, may be represented by the following formulas (I-2-a) and (I-2-b):

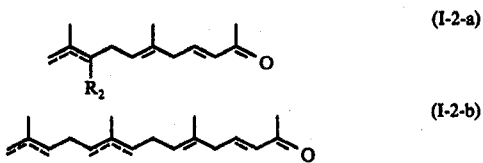

In the formula (I-2-a), the dotted line and $R_2$ have the same meanings as respectively defined for the formula (I-1-a), while in the formula (I-2-b), the dotted line is as defined for the formula (I-1-b).

Thus, it is often desired to isomerize a ketone of formula (I-2-a) which is produced in admixture with a ketone of formula (I-1-a), or a ketone of formula (I-2-b) which is produced in admixture with a ketone of formula (I-1-b) in order to obtain the $\alpha.\beta,\gamma.\delta$-unsaturated ketones of formula (I-1-a) or of formula (I-1-b). For such purposes, the use of a rhodium compound, a ruthenium compound, iodine-containing ammonium compound, a bromine-containing ammonium compound or iodine is effective as an isomerization catalyst in the practice of this invention.

It is known that the isomerization of an unconjugated ketone to a conjugated ketone is catalyzed by an acid or an alkaline compound such as an inorganic or organic acid, the hydroxide or carbonate of an alkali metal or alkaline earth metal. However, it is undesirable to use such acids or alkaline compounds as a catalyst in the isomerization of $\alpha.\beta,\delta.\epsilon$-unsaturated ketones to $\alpha.\beta,\gamma.\delta$-unsaturated ketones because of their instability against strong acids or alkaline compounds.

The most desirable examples of the aforementioned compounds which can be used as isomerization catalysts according to this invention are rhodium chloride hydrates, ammonium iodide, hydrogen iodide salts of amines, and iodine. The amines include primary, secondary and tertiary mono- and polyamines, both cyclic and acyclic.

Being not as highly effective as the aforesaid catalysts, tris (triphenylphosphine) rhodium chloride, tris (triphenylphosphine) ruthenium chloride, rhodium acetylacetonate, ruthenium acetylacetonate, ruthenium chloride hydrates, tri (pyridine) rhodium chlorides, ammonium bromide and hydrogen bromide salts of amines may also be used as isomerization catalysts.

Within the present invention, said isomerization reaction may be applied to the separated unsaturated ketones of formula (I-2-a) or of formula (I-2-b). It may also be applied to a mixture of an unsaturated ketone of formula (I-2-a) and an unsaturated ketone of formula (I-1-a) as well as to a mixture of unsaturated ketones of formula (I-2-b) and formula (I-1-b). While the amount of said isomerization catalyst is not strictly critical, it is preferable to use an amount of at least about 0.05 percent by weight relative to the unsaturated ketone of formula (I-2-a or b) for the purpose of expediting the reaction. On the other hand, in order to provide for a maximum reaction rate it seems unnecessary to use more than about 10 weight percent of the catalyst based on the unsaturated ketone of formula (I-2-a or b). It is recommended, for practical purposes, to use 0.1 to 2 weight percent of the isomerization catalyst relative to the unsaturated ketone of formula (I-2a or b). The reaction temperature may be as low s 0° C. and as high as 250° C., but considering the thermal stability of the starting material and the resulting unsaturated ketones, as well as the rate and selectivity of the reaction, it is preferable to conduct the reaction at temperatures of between 50° C. and 200° C. The reaction may be carried out under atmospheric, elevated or reduced pressure.

The isomerization catalyst which is used according to the present invention has no adverse effect on the rearrangement reaction of the starting substituted propargyl alcohol. Therefore, the rearrangement reaction of a substituted propargyl alcohol, e.g., an alcohol represented by formula (II-a) or (II-b) and the isomerization of a ketone of formula (I-2-a) or (I-2-b) which is contained in the formed mixture of unsaturated ketones may be carried out in the same reaction system simultaneously since in a certain temperature range, both reactions take place with satisfactory speed. The advantage of the isomerization reaction according to this invention is best realized under such above mentioned conditions. Thus, by the rearrangement reaction under the conditions of isomerization, the $\alpha.\beta,\gamma.\delta$-unsaturated ketones of formula (I-1-a) and formula (I-1-b) can be directly produced from the substituted propargyl alcohols of formula (II-a) and formula (II-b), respectively, in most satisfactory yields.

The isomerization reaction according to this invention does not necessarily require a solvent or diluent. However, diluents can be used insofar as they are stable under the conditions of reaction and per se will not be involved in the reaction. Examples of such diluents are methanol, ethanol, benzene, toluene, xylene, dimethylacetamide and N-methylpyrrolidone. Where an isomerization reaction is carried out in the same reaction system as the rearrangement of the substituted propargyl alcohol of formula (II-a) or formula (II-b) as mentioned above, such an additive has to be used which does not interfere with the isomerization reaction and is suited to the rearrangement reaction. Studies on this point have shown that a polar organic compound containing an amido group

or a phosphoryl group

is suitable for the purpose. Those organic compounds do not influence the isomerization reaction but enhance the selectivity for the conversion of the substituted propargyl alcohols of formula (II-a) and formula (II-b) to the corresponding unsaturated ketones.

The amount of the additive which is used for this purpose is similar to the amount mentioned in connection with the rearrangement reaction in the absence of an isomerization catalyst. The amount of isomerization catalyst in this embodiment of the invention is also similar to that mentioned hereinbefore.

In summary, a preferable embodiment of the method for producing unsaturated ketones according to the present invention comprises a step of producing a mixture of unsaturated ketones of formula (I-1-a) and of formula (I-2-a) or a mixture of unsaturated ketones of formula (I-1-b) and of formula (I-2-b) through the rearrangement of the substituted propargyl alcohol of formula (II-a) or formula (II-b) and a step of isomerizing the unsaturated ketone of formula (I-2-a) or formula (I-2-b) to the unsaturated ketone of formula (I-1-a) or formula (I-1-b) in the presence of a catalyst, said two steps being performed in independent reaction systems or in a single reaction system.

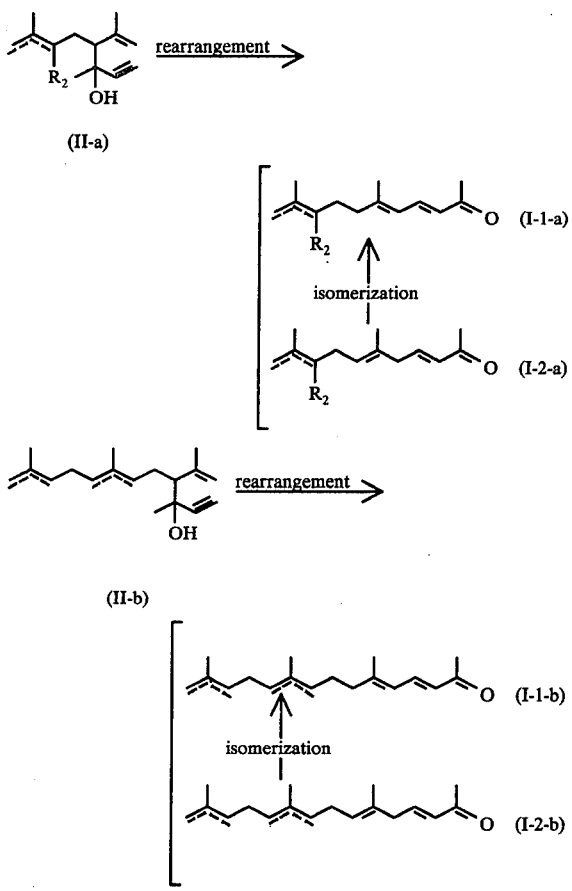

A first example of the unsaturated ketone which is particularly desirable to be produced by the above method is 6,10-dimethyl-3,5,9-undecatrien-2-one

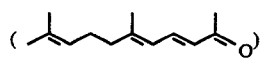

which is obtained from 4-isopropenyl-3,7-dimethyl-1-octyn-6-en-3-ol. This unsaturated ketone may be cyclized in the presence of an acid catalyst to ionone which is of value of a perfumery product or as an intermediate for the production of vitamin A and colorants. A second example is 6,9,10-trimethyl-3,5,9-undecatrien-2-one

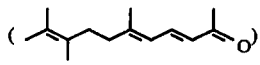

which is obtained from 4-isopropenyl-3, 6,7-trimethyl-1-octyn-6-en-3-ol. This unsaturated ketone is of value as an intrmediate for the production of irone. The following are some other α. β,γ.δ-unsaturated ketones which are preferably produced by the method described above.

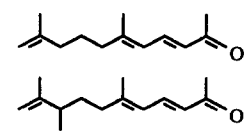

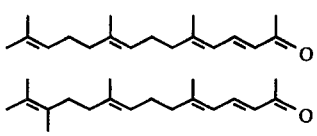

It should be understood that the chemical formulas given hereinbefore and hereinafter are not intended to designate the stereospecific structures of the compounds.

The invention will now be described by the following examples which are intended to be illustrative and in no wise limitative.

EXAMPLE 1

(1) Production of the α,β- and β,γ-unsaturated ketones

To a solution of 600 g of sodium hydroxide in 490 g of water was added 980 g of mesityl oxide together with 520 g of prenyl chloride and 25 g of trimethylstearylammonium chloride, and the mixture was reacted in a water bath under stirring for 2 hours (The reaction temperature rose to 70° C.). The reaction mixture was poured into water and extracted with ethyl ether. The ethereal solution was washed with water and dried over anhydrous sodium sulfate. The ether was distilled off under reduced pressure and the residue (1250 g) was further distilled to recover the unreacted mesityl oxide. Thereupon, as higher-boiling products, 560 g of a 2.5:1 mixture of 3-isopropenyl-6-methyl-5-hepten-2-one and 3-isopropylidene-6-methyl-5-hepten-2-one (purity 96.4%) was obtained. Based on the purity of 83.71% for the prenyl chloride used, the yield of 3-isopropenyl-6-methyl-5-hepten-2-one was 59% (410 g) and that of 3-isopropylidene-6-methyl-5-hepten-2-one was 19% (130 g).

The above mixture of unsaturated ketones was distilled in a rectifying column with 30 theoretical plates, whereby 3-isopropenyl-6-methyl-5-hepten-2-one was obtained from a forerunning distillate at bp. 32°–34° C./0.2 mmHg, and 3-isopropylidene-6-methyl-5-hepten-2-one being obtained from the after-running distillate at bp. 35°–38° C./0.2 mmHg. The structural identification of these ketones was performed by the following methods.

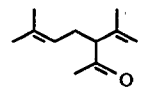

Infrared absorption spectrum: (cm$^{-1}$) 1714(>C=O), 1642 (>C=C<), 1445, 1378, 1353, 1153, 900

| Nuclear magnetic resonance spectrum ($\delta_{ppm}^{in\,CCL_4}$): | |
|---|---|
| 1.57, 1.58 | (each s, 9H, CH$_3$—) |
| 1.99 | (s, 3H, CH$_3$C—) ‖ O |
| 2.03 – 2.40 | (m, 2H, —CH$_2$—) |
| 3.07 | (t, 1H, —C—CH<) ‖ O |
| 4.85, 4.89 | (each s, 2H, =CH$_2$) |
| 4.95 | (t, 1H, =CH—) |

-continued

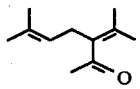

Infrared absorption spectrum (cm$^{-1}$): 1688(>C=O), 1615 (>C=C<), 1440, 1375, 1350, 1278, 1202, 1170, 975, 935, 850

Nuclear magnetic resonance spectrum ($\delta_{ppm}^{in CCL_4}$):

| | |
|---|---|
| 1.62, 1.70, 1.75 | (each s, 12H, CH$_3$—) |
| 2.05 | (s, 3H, CH$_3$C(=O)—) |
| 2.88 | (d, 2H, —CH$_2$—) |
| 4.97 | (t, 1H, —CH=C<) |

(2) Isomerization of the α,β-unsaturated ketone

Together with 7 g of trans-1-2-cyclohexanedicarboxylic acid, the above 3-isopropylidene-6-methyl-5-hepten-2-one (130 g) was fed into the bottom of a rectifying column with 50 theoretical plates and distillation was carried out at a reduced pressure of 30 mmHg with a reflux ratio of 30:1, whereby 107 g of distillate was obtained. Gas chromatographic analysis of this distillate revealed that it was a mixture of 3-isopropenyl-6-methyl-5-hepten-2-one (94%) and 3-isopropylidene-6-methyl-5-hepten-2-one (6%). The product was combined with 410 g of 3-isopropenyl-6-methyl-5-hepten-2-one previously obtained and was subjected to the following ethynylation reaction.

(3) Production of the substituted propargyl alcohol

In a three-necked flask of 5-liter capacity, 70 g of sodium metal was added to 3 liter of liquid ammonia and acetylene gas was bubbled through this mixture. At the moment when the reaction mixture turned gray, the introduction of acetylene gas was suspended and 517 g of the 3-isopropenyl-6-methyl-5-hepten-2-one (containing a small amount of 3-isopropylidene-6-methyl-5-hepten-2-one) was added. Under acetylene gas bubbling, the reaction was continued at −33° C. for 3 hours. Subsequent to the removal of the ammonia, the reaction mixture was neutralized with ammonium chloride, poured into water and extracted with ether. The ethereal solution was dried over sodium sulfate and the solvent was distilled off under reduced pressure. The residue weighing 524 g was distilled under reduced pressure to recover 519 g of a distillate at bp. 59°–61° C./0.5 mmHg. This distillate was a mixture of 3-isopropenyl-6-methyl-5-hepten-2-one (2 wt. %), 3-isopropylidene-6-methyl-5-hepten-2-one (8 wt. %) and 4-isopropenyl-3,7-dimethyl-6-octen-1-yn-3-ol (90 wt. %). The structural identification of the main product was carried out by the following methods.

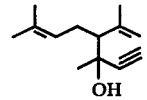

Infrared absorption spectrum (cm$^{-1}$): 3440(—OH), 3300, 2120, 1640, 1450, 1378, 1128, 1030, 900

Nuclear magnetic resonance spectrum ($\delta_{ppm}^{in CCL_4}$):

| | |
|---|---|
| 1.40 | (s, 3H, CH$_3$—C(—O—)—) |
| 1.60 | (s, 6H, CH$_3$—) |
| 1.72, 1.73 | (each s, 3H, CH$_3$—) |
| 2.00 – 2.47 | (m, 3H, —CH$_2$—CH—) |
| 2.30 | (s, 1H, —C≡CH) |
| ca, 4.83 – 5.00 | (m, 3H, =CH—, =CH$_2$) |

(4) Production of the α,β,γ,δ- and α,β,δ,ε-unsaturated ketones

In a three-necked flask of 500 ml capacity, 197 g (purity 90%) of 4-isopropenyl-3,7-dimethyl-6-octen-1-yn-3-ol is heated in a nitrogen gas atmosphere at an internal temperature of 150° C. for 10 hours. The rearrangement reaction mixture thus obtained is directly distilled in vacuo to recover 101 g of a low-boiling fraction containing the unreacted starting material (b.p. 76° C. and less/0.16–0.17 mmHg) and 70 g of a high-boiling fraction consisting of the rearrangement products 6,10-dimethyl-3,5,9-undecatrien-2-one and 6,10-dimethyl-3,6,9-undecatrien-2-one (purity 94.7%) (b.p. 76 - 92° C./0.16 - 0.17 mmHg). The structure of the rearrangement product was identified in the following manner. The above mixture was separated and resolved into two components by gas chromatography. One of the components was identified as 6,10-dimethyl-3,5,9-undecatrien-2-one because of the agreement of its infrared absorption and nuclear magnetic resonance spectra with those of an authentic commercial sample of the compound. For additional proof, the same component was reacted in the presence of the phosphoric acid catalyst in the conventional manner and, based on the formation of α-ionone and β-ionone, it was identified as 6,10-dimethyl-3,5,9-undecatrien-2-one. The other component was established to be 6,10-dimethyl-3,6,9-undecatrien-2-one by the following methods.

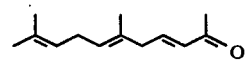

Infrared absorption spectrum (cm$^{-1}$): 1675, 1623, 1440, 1376, 1360, 1255

Nuclear magnetic resonance spectrum ($\delta_{ppm}^{CCl_4}$): 1.60 (s, 9H), 2.11 (s, 3H), 2.72 (m, 4H), 5.01 (m, 1H), 5.12 (m, 1H), 5.94 (m, 1H), 6.40-6.90 (m, 1H)

EXAMPLE 2

(1) Production of the α,β- and β,γ-unsaturated ketones

The procedure of Example 1 (Production of the α,β- and β,γ-unsaturated ketones) was repeated except that 590 g of 2,3-dimethyl-1-chloro-2-butene was employed in lieu of 520 g of prenyl chloride. The reaction mixture was poured into water and extracted with ether. The ethereal solution was washed with water and dried over anhydrous sodium sulfate. The solvent was removed from the ethereal solution under reduced pressure and the residue was distilled to recover the unreacted mesityl oxide. As a highboiling fraction (b.p. 92.0°–92.5° C./5.5 mmHg), there was obtained 730 g of a 6:1 mixture of 3-isopropenyl-5,6-dimethyl-5-hepten-2-one and 3-isopropylidene-5,6-dimethyl-5-hepten-2-one. The structural identity of the former product was established by the following methods.

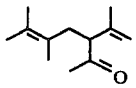

Infrared absorption spectrum (cm⁻¹): 3070, 1712 (>C=O), 1640 (>C=C<), 1445, 1373, 1350, 1152, 898

| Nuclear magnetic resonance spectrum ($\delta_{ppm}^{inCCl_4}$): | |
|---|---|
| 1.51, 1.54, 1.57, 1.58 | (s, 12H, $CH_3$—) |
| 1.93 | (s, 3H, $CH_3C$—) ‖ O |
| 1.88 – 2.55 | (m, 2H, —$CH_2$—) |
| 3.13 | (t, 1H, —C—CH<) ‖ O |
| 4.73 | (s, 2H, =$CH_2$) |

(2) Production of the substituted propargyl alcohol

The procedure of Example 1 (Production of the substituted propargyl alcohol) was repeated except that 560 g of 3-isopropenyl-5,6-dimethyl-5-hepten-2-one (containing a small amount of 3-isopropylidene-5,6-dimethyl-5-hepten-2-one) was employed in lieu of 517 g of 3-isopropenyl-6-methyl-5-hepten-2-one. Following the removal of ammonia, this ethynylation reaction mixture was neutralized with ammonium chloride, poured into water and extracted with ether. The ethereal solution was dried over anhydrous sodium sulfate and distilled under reduced pressure to remove the solvent. The residue was further distilled under reduced pressure to recover 585 g of a distillate at 89°–92° C./2.3 mmHg. This distillate was found to be a mixture of 3-isopropenyl-5,6-dimethyl-5-hepten-2-one (3.5 wt. %), 3-isopropylidene-5,6-dimethyl-5-hepten-2-one (12.5 wt. %) and 4-isopropenyl-3,6,7-trimethyl-1-octyn-6-en-3-ol (84 wt. %). The structural identity of the main ethynylation product was established by the following methods.

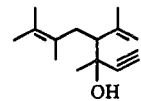

Infrared absorption spectrum (cm⁻¹): 3440 (—OH), 3300, 3070, 1639, 1450, 1375, 900

| Nuclear magnetic resonance spectrum ($\delta_{ppm}^{inCCl_4}$): | |
|---|---|
| 1.41 | (s, 3H, $CH_3$—C—) ‖ O— |
| 1.56 | (s, 9H, $CH_3$—) |
| 1.74 | (each s, 3H, $CH_3$—) |
| 2.21 – 2.45 | (m, 3H, —$CH_2$—CH—) |
| 2.31 | (s, 1H, —C≡CH) |
| 4.86 | (s, 2H, =$CH_2$) |

(3) Production of the α,β-, γ,δ- and α,β,δ,ε-unsaturated ketones

In a three-necked flask of 500 ml capacity, 226 g of the above 4-isopropenyl-3,6,7-trimethyl-1-octyn-6-en-3-ol (purity 84%) was subjected to a rearrangement reaction by heating it in a nitrogen atmosphere at an internal temperature of 165° C. for 4 hours. The reaction mixture was directly distilled in vacuo to remove a lowboiling fraction containing the unreacted starting material. As a highboiling distillate (b.p. 103-105° C./0.7 mmHg), there was obtained 101 g of a mixture of the desired product 6,9,10-trimethyl-3,5,9-undecatrien-2-one and 6,9,10-trimethyl-3,6,9-undecatrien-2-one (purity 93%). Each of these compounds was a 3:7 mixture of cis- and trans- isomers. The structural identity was established as follows.

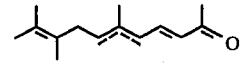

Infrared absorption spectrum (cm⁻¹): 1718, 1668, 1630, 1587, 1440, 1376, 1360, 1255, 1156, 970, 885

The characteristic fragments of the mass spectra of 6,9,10-trimethyl-3,5,9-undecatrien-3-one and 6,9,10-trimethyl-3,6,9-undecatrien-2-one differ in that whereas the former gives intense peaks at m/e 124, 109, 83, 55, 43 and 41 (100%), the latter has a main fragment at m/e 43 (100%).

EXAMPLES 3 to 13

The α,β,γ,δ- and α,β,δ,ε-unsaturated ketones (I) were produced by a process comprising the step of condensing one of various organic halides (R-halo) with mesityl oxide to obtain an α,β-unsaturated ketone (IV) and a β,γ-unsaturated ketone (III), the step of ethynylating the β,γ-unsaturated ketone which has been isolated, and the step of heating the resultant substituted propargyl alcohol (II) to effect a rearrangement of the same. The results are set forth in Table I.

TABLE I-1

| | R-halo | | Mesityl | | Yield (%) of the formed ketones (III)+(IV) | Mole ratio (III)/(IV) |
|---|---|---|---|---|---|---|
| EX. | Type | Amount (mol.) | oxide (mol.) | Reaction conditions | | |
| 3 | ![structure: isobutyl bromide derivative]—Br | 2.0 | 4.0 | Sodium (2.0 mol.) in ammonia Ferric chloride catalyst, −33° C, 6 hrs. | 80 | 89/11 |
| 4 | ![structure with OH]—Br | 2.0 | 4.0 | Sodium (2.0 mol.) in ammonia Ferric chloride catalyst, −33° C, 6 hrs. | 62 | 88/12 |
| 5 | ![structure with =CH2]—Br | 2.0 | 4.0 | Sodium (2.0 mol.) in ammonia Ferric chloride catalyst, −33° C, 6 hrs. | 65 | 89/11 |
| 6 | ![structure]—Cl | 1.0 | 1.8 | Sodium (1.1 mol.) in ammonia Ferric chloride catalyst, −33° C, 6 hrs. | 80 | 90/10 |
| 7 | ![structure with OCH3]—Cl | 1.0 | 1.8 | Sodium (1.1 mol.) in ammonia Ferric chloride catalyst, −33° C, 6 hrs. | 58 | 90/10 |
| 8 | ![geranyl bromide]—Br | 2.0 | 4.0 | 55% aqueous solution of NaOH (3 mol.), Trimethylstearylammonium chloride, 35° C, 2 hrs. | 86 | 75/25 |
| 9 | ![structure]—Cl | 1.0 | 3.0 | 55% aqueous solution of NaOH (2 mol.), Trimethylstearylammonium chloride, 35–40° C, 3 hrs. | 83 | 73/27 |
| 10 | ![structure]—Cl | 1.0 | 3.0 | 55% aqueous solution of NaOH (2 mol.), Trimethylstearylammonium chloride, 35–40° C, 3 hrs. | 80 | 75/25 |
| 11 | ![structure]—Br | 1.0 | 2.5 | 55% aqueous solution of KOH (2.0 mol.), Trimethylstearylammonium chloride, 40° C, 2 hrs. | 84 | 77/23 |
| 12 | ![structure]—Cl | 1.0 | 2.5 | 55% aqueous solution of KOH (2.0 mol.), Trimethylstearylammonium chloride, 40° C, 2 hrs. | 81 | 78/22 |
| 13 | ![structure with OH]—Br | 1.0 | 4.0 | Sodium (1.0 mol.) in ammonia, Ferric chloride catalyst, −33° C, 3 hrs. | 72 | 91/9 |

TABLE I-2

Ethynylation reaction of the β,γ-unsaturated ketone (III)

| | | Formed propargyl alcohol (II) | |
|---|---|---|---|
| EX. | Reaction conditions | Type | Yield (%) based on (III) |
| 3 | Sodium (1.4 mol.) in ammonia, Released system | ![structure with OH and alkyne] | 92 |
| 4 | Sodium (1.4 mol.) in ammonia, Released system | ![structure with two OH and alkyne] | 91 |
| 5 | Sodium (1.4 mol.) in ammonia, Released system | ![structure with OH and alkyne] | 93 |

TABLE I-2-continued

Ethynylation reaction of the β.γ-unsaturated ketone (III)

| EX. | Reaction conditions | Formed propargyl alcohol (II) Type | Yield (%) based on (III) |
|---|---|---|---|
| 6 | Sodium (0.7 mol.) in ammonia, Released system | (structure) | 93 |
| 7 | Sodium (0.7 mol.) in ammonia, Released system | (structure with OCH$_3$) | 85 |
| 8 | KOH (1 wt. %) in ammonia at 0–5° C for 5 hrs. in autoclave | (structure) | 90 |
| 9 | KOH (1 wt. %) in N-methylpyrrolidone at 0–3° C for 5 hrs. in autoclave | (structure) | 91 |
| 10 | KOH (1 wt. %) in N-methylpyrrolidone at 0–3° C for 5 hrs. in autoclave | (structure) | 91 |
| 11 | KNH$_2$ (0.5 wt. %) in ammonia at 3–6° C for 5 hrs. in autoclave | (structure) | 93 |
| 12 | KNH$_2$ (0.5 wt. %) in ammonia at 3–6° C for 5 hrs. in autoclave | (structure) | 92 |
| 13 | KOH (1 wt. %) in dimethylformamide at −2−+3° C for 5 hrs. in autoclave | (structure with OH) | 90 |

TABLE I-3

Rearrangement of the propargyl alcohol (II)

| Example | Reaction conditions | Formed unsaturated ketones (I) Type | Yield (%) based on (II) |
|---|---|---|---|
| 3 | 150° C, 10 hrs. | (structure) | 53 |
| 4 | 165° C, 4 hrs. | (structure with OH) | 51 |
| 5 | 165° C, 4 hrs. | (structure) | 55 |
| 6 | 150° C, 10 hrs. | (structure) | 44 |
| 7 | 165° C, 4 hrs. | (structure) | 48 |
| 8 | 185° C, 2 hrs. | (structure with OCH$_3$) | 37 |

TABLE I-3-continued

Rearrangement of the propargyl alcohol (II)

| Example | Reaction conditions | Formed unsaturated ketones (I) Type | Yield (%) based on (II) |
|---|---|---|---|
| 9 | 185° C, 2 hrs. | (structure) | 30 |
| 10 | 165° C, 4 hrs. | (structure) | 53 |
| 11 | 185° C, 2 hrs. | (structure) | 35 |
| 12 | 165° C, 4 hrs. | (structure) | 53 |
| 13 | 185° C, 2 hrs. | (structure with OH) | 40 |

EXAMPLE 14

120 ml of 4-isopropenyl-3,7-dimethyl-1-octyn-6-en-3-ol was mixed with 240 ml of dimethylsulfoxide and, in a nitrogen atmosphere, the mixture was maintained at 165° C. for 4 hours. The reaction mixture was directly distilled in vacuo to remove a low-boiling fraction containing the dimethylsulfoxide and unreacted starting material. Then, as a high-boiling fraction at b.p. 80.5°–89.5° C./0.15 mmHg, a mixture of 6,10-dimethyl-3,5,9-undecathien-2-one and 6,10-dimethyl-3,6,9-undecatrien-2-one was obtained in a yield of 68.2% with a selectivity of 73.7%. When the reaction was conducted in the absence of dimethylsulfoxide and at 150° C. for 7 hours, the yield of the intended product was 38.2% with a selectivity of 51.1%.

EXAMPLE 15

A 1:1 (V/V) mixture of 4-isopropenyl-3,7-dimethyl-1-octyn-6-en-3-ol and dimethylsulfoxide was heated as in Example 14 to obtain as a rearrangement product a mixture of 6,10-dimethyl-3,5,9-undecatrien-2-one and 6,10-dimethyl-3,6,9-undecatrien-2-one in a yield of 66.7% with a selectivity of 70.9%.

EXAMPLE 16

A 1:3 (V/V) mixture of 4-isopropenyl-3,7-dimethyl-1-octyn-6-en-3-ol and dimethylsulfoxide was heated as in Example 14 to obtain the intended mixture of unsaturated ketones in a yield of 69.6% with a selectivity of 75.5%.

EXAMPLES 17 AND 18

5 ml of 4-isopropenyl-3,7-dimethyl-1-octyn-6-en-3-ol was mixed with 5 ml or 15 ml of N-methylpyrrolidone and, in a nitrogen atmosphere, the reaction was carried out at a temperature of 165° C. for 4 hours. The contents of the resultant mixture of 6,10-dimethyl-3,5,9-undecatrien-2-one and 6,10-dimethyl-3,6,9-undecatrien-2-one was determined by gas chromatography (PEG 20M, column temp. 170° C.) (internal reference method). The results are shown in Table 2.

TABLE II

| Example | Amount of N-methylpyrrolidone used(ml) | Yield (%) | Selectivity (%) |
|---|---|---|---|
| 17 | 5 | 64.0 | 66.9 |
| 18 | 15 | 67.6 | 70.5 |

EXAMPLE 19

A three-necked flask of 1000 ml capacity was charged with 226 g of 4-isopropenyl-3,6,7-trimethyl-1-octyn-6-en-3-ol (purity 84%), which was prepared in the same manner as in Example 2, and 470 ml of dimethylsulfoxide. In a nitrogen atmosphere, the mixture was heated to an internal temperature of 150° C. for 10 hours to accomplish a rearrangement of the starting compound. The reaction product was directly distilled in vacuo to remove a low-boiling fraction of the dimethylsulfoxide and unreacted starting material. Thereafter, as a high-boiling fraction (b.p. 103°–105° C./0.7 mmHg), there was obtained 132 g of a 1:1 mixture of the intended products 6,9,10-trimethyl-3,5,9-undecatrien-2-one and 6,9,10-trimethyl-3,6,9-undecatrien-2-one (purity 93%). Each of them was a 3:7 mixture of cis- and trans- isomers.

EXAMPLES 20 TO 30

In a nitrogen atmosphere, a mixture of 5 ml of 4-isopropenyl-3,7-dimethyl-1-octyn-6-en-3-ol and 15 ml of one of the various additives listed in Table III were maintained at 165° C. for 4 hours. The content of the rearrangement product mixture of 6,10-dimethyl-3,5,9-undecatrien-2-one and 6,10-dimethyl-3,6,9-undecatrien-2-one was determined by gas chromatography (PEG 20M, column temp. 170° C.) (internal reference method). The results are set forth in Table III.

TABLE III

| Example | Additive | Yield (%) | Selectivity (%) |
|---|---|---|---|
| 20 | Diethylsulfoxide | 67.6 | 73.4 |
| 21 | Tetramethylene sulfoxide | 70.1 | 75.0 |
| 22 | Dimethylformamide* | 61.7 | 68.6 |
| 23 | Dimethylacetamide | 63.3 | 70.9 |
| 24 | Diethylformamide | 63.8 | 69.3 |
| 25 | Diethylacetamide | 63.7 | 69.8 |
| 26 | Pyrrolidone | 66.5 | 71.1 |
| 27 | ε-Caprolactam | 62.7 | 68.8 |
| 28 | Trimethyl phosphate | 59.2 | 65.2 |
| 29 | Triethyl phosphate | 57.5 | 64.0 |

TABLE III-continued

| Example | Additive | Yield (%) | Selectivity (%) |
|---|---|---|---|
| 30 | Hexamethylphosphoramide | 70.0 | 71.0 |

*In Example 22 only, the reaction was conducted at 150° C for 10 hrs.

EXAMPLES 31 TO 34

In a nitrogen atmosphere, a mixture of 5 ml of 4-isopropenyl-3,6,7,-trimethyl-1-octyn-6-en-3-ol and 15 ml of one of the additives indicated in Table IV was maintained at 165° C. for 4 hours to effect a rearrangement reaction of the starting material. The yields and selectivity values of the products 6,9,10-trimethyl-3,5,9-undecatrien-2-one and 6,9,10-trimethyl-3,6,9-undecatrien-2-one are shown in Table IV.

TABLE IV

| Example | Additive | Yield (%) | Selectivity (%) |
|---|---|---|---|
| 31 | N-methylpyrrolidone | 66.9 | 73.5 |
| 32 | Pyrrolidone | 65.4 | 72.4 |
| 33 | Dimethylacetamide | 66.9 | 72.3 |
| 34 | Trimethyl phosphate | 63.6 | 69.5 |

EXAMPLE 34

(1) Production of the $\alpha.\beta$- and $\beta.\gamma$-unsaturated ketones

In a solution of 99.6 g of sodium hydroxide in 81.5 g of water and in the presence of 5 g of methyl tricyclohexyl sulfonium chloride, 142.8 g of geranyl chloride was reacted with 162.7 g of isomesityl oxide (purity 98.4%) at 40° C. for 4 hours. The reaction mixture was poured into water and extracted with ether. The ethereal solution was washed with water and dried over anhydrous sodium sulfate. Thereafter, the ether, unreacted isomesityl oxide and isomerization product mesityl oxide were distilled off under reduced pressure. The residue, weighing 188 g, was distilled in vacuo to recover 164 g of a mixture of 3-isopropenyl-6,10-dimethyl-5,9-undecadien-2-one (58%) and 3-isopropylidene-6,10-dimethyl-5,9-undecadien-2-one (42%) as a distillate at b.p. 80°-98° C./0.2 mmHg. This mixture was rectified to recover, as a fraction boiling at 84°-89° C./0.25 mmHg, 76 g of 3-isopropenyl-6,10-dimethyl-5,9-undecadien-2-one and, as a fraction boiling at 93°-97° C./0.25 mmHg, 47 g of 3,isopropylidene-6,10-dimethyl-5,9-undecadien-2-one together with 34 g of an intermediate-boiling fraction.

(2) Production of the substituted propargyl alcohol

An autoclave was charged with 76 g of 3-isopropenyl-6,10-dimethyl-5,9-undecadien-2-one, 1000 ml of liquid ammonia and, as a catalyst, a solution of 1.3 g of potassium hydroxide in 5 ml of water, and acetylene gas was bubbled into the mixture to a total pressure at −5° C. of 6.7 kg/cm². The reaction mixture was neutralized with ammonium chloride, and following the removal of ammonia, the residue was poured into water and extracted with ether. The ethereal solution was dried over anhydrous sodium sulfate and, then, is distilled under reduced pressure to remove the solvent. The residue was further distilled under reduced pressure to recover 77.4 g of a fraction at b.p. 120°-125° C./0.3 mmHg. Gas chromatographic analysis of this distillate showed that it was a mixture of 3-isopropenyl-6,10-dimethyl-5,9-undecadien-2-one (3.6 wt. %), 3-isopropylidene-6,10-dimethyl-5,9-undecadien-2-one (12.3 wt. %) and 4-isopropenyl-3,7,11-trimethyldodeca-6,10-dien-1-yn-3-ol (84.1 wt. %). The structural identity of the main ethynylation product was established as follows.

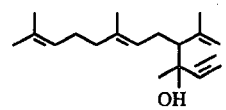

OH

Infrared absorption spectrum (cm⁻¹): 3500, 3450, 3290, 1630, 1442, 1373, 1125, 1025, 942, 920, 895

| Nuclear magnetic resonance spectrum (in CCl₄;ppm) | |
|---|---|
| 1.40 | (s, 3H, CH₃—) |
| 1.53, 1.58, 1.75 ca 1.87–2.50 | (s, 12H, CH₃—) |
| 2.30 | (m, 7H, —CH₂—CH₂—, —CH₂ĊH—) |
| | (s, 1H, —C≡CH) |
| ca 4.75–5.15 | (m, 4H, =CH₂, =CH—) |

(3) Production of the $\alpha.\beta,\delta.\epsilon$-unsaturated ketone

In a three-necked flask of 200 ml capacity, a mixture of 26.2 g of 4-isopropenyl-3,7,11-trimethyldodaca-6,10-dien-1-yn-3-ol (purity 84.1%) and 90 ml of N-methylpyrrolidone was maintained at a temperature of 165° C. and in a nitrogen atmosphere for 4 hours. The reaction mixture was directly distilled in vacuo to recover 15.2 g of a high-boiling fraction predominantly consisting of 6,10,14-trimethyl-3,6,9,13-pentadecatetraen-2-one (b.p. 134°–138° C./0.49 mmHg).

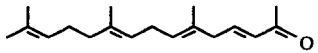

Infrared absorption spectrum (cm⁻¹): 2960, 2920, 2850, 1715, 1680, 1620, 1440, 1375, 1355, 1155, 965

EXAMPLE 35

(1) Production of the $\alpha.\beta,\gamma.\epsilon$- and $\alpha.\beta,\delta.\epsilon$-unsaturated ketones A three-necked flask of 300 ml capacity was charged with 48 g of 4-isopropenyl-3,7-dimethyl-1-octyn-6-en-3-ol and 160 ml of N-methylpyrrolidone and, in a nitrogen atmosphere, the mixture was maintained at 165° C. with stirring for 4 hours. The reaction mixture was directly distilled to recover 30.2 g of a mixture of 6,10-dimethyl-3,6,9-undecatrien-2-one [designated (I-2)] and 6,10-dimethyl-3,5,9-undecatrien-2-one [designated (I-1)]. The ratio of (I-2) to (I-1) was 93.2:6.8.

(I-2) Infrared absorption spectrum (cm⁻¹): 2960, 2920, 2850, 1715, 1675, 1623, 1440, 1360, 1255, 1160, 1110, 970

(I-1) Infrared absorption spectrum (cm⁻¹): 2960, 2910, 2820, 1660, 1625, 1585, 1440, 1360, 1250, 1155, 970, 885

(2) Isomerization of the $\alpha.\beta,\delta.\epsilon$-unsaturated ketone

A three-necked flask of 20 ml capacity was charged with 5 ml of the above ketone mixture, 5 ml of ethanol and 0.2 or 0.5 weight %, based on the ketone mixture, of iodine (0.009 g or 0.022 g), and the isomerization reaction was conducted at the reflux temperature of ethanol with stirring. The changing of the ratio of (I-2) to (I-1) in the reaction mixture was determined relative to the reaction period by gas chromatography (PEG 20 M, column temp. 170° C.). The results are set forth in Table V.

TABLE V

| Reaction time (hrs.) | Amount of iodine, 0.2 wt. % (I-2):(I-1) ratio | Amount of iodine, 0.5 wt. % (I-2)-(I-1) ratio |
| --- | --- | --- |
| 0.5 | — | 10.1 : 89.9 |
| 1 | 75.8 : 24.2 | 8.4 : 91.6 |
| 2 | 54.0 : 46.0 | 7.1 : 92.9 |
| 3 | 33.5 : 66.5 | 6.4 : 93.6 |
| 4 | 24.2 : 75.8 | 5.9 : 94.1 |
| 5 | 18.6 : 81.4 | 5.7 : 94.3 |

EXAMPLES 36 TO 42

Using 5 ml of a mixture (I-2)/(I-1)=93.2/6.8 of 6,10-dimethyl-3,6,9-undecatrien-2-one (I-2) and 6,10-dimethyl-3,5,9-undecatrien-2-one (I-1), the isomerization reaction was carried out under the conditions indicated in Table VI. The results are summarized in Table VI.

TABLE VI

| Example | Catalyst Type | Amount (wt.%) | Solvent Type | Amount (ml) | Reaction time (hrs.) | Reaction temp. (°C) | (I-2): (I-1): ratio |
| --- | --- | --- | --- | --- | --- | --- | --- |
| 36 | Iodine | 0.5 | — | 0 | 5 | 70 | 22.9:77.1 |
| 37 | Ammonium iodide | 1 | N-methylpyrrolidone | 15 | 3 | 165 | 5.3:94.7 |
| 38 | Rhodium trichloride (trihydrate) | 0.5 | Ethanol | 10 | 3 | Reflux | 5.5:94.5 |
| 39 | Tris(triphenylphosphine) rhodium chloride | 0.5 | Toluene | 10 | 2 | 100 | 45.2:54.8 |
| 40 | Tris(triphenylphosphine) ruthenium chloride | 0.5 | Toluene | 10 | 2 | 100 | 70.3:29.7 |
| 41 | Dimethylaniline hydrogen iodide | 1 | N-methylpyrrolidone | 15 | 3 | 165 | 5.1:94.9 |
| 42 | Ammonium bromide | 3 | Ethanol | 10 | 4 | Reflux | 61.5:38.5 |
| Control Ex. 1 | 85% Phosphoric acid | 0.1 (ml) | Ethanol | 1 | 0.5 | Reflux | Isomerization rate=5.9% |
| 2 | 10% Aqueous potassium carbonate | 0.5 (ml) | Ethanol | 1 | 0.5 | Reflux | Isomerization rate-ca 0% |
| 3 | Sodium ethoxide | 0.01 (g) | Ethanol | 1 | 3.0 | Room temp. | Isomerization rate=1.5% |

EXAMPLE 43

In a nitrogen atmosphere, a mixture of 10 ml of 4-isopropenyl-3,6,7-trimethyl-1-octyn-6-en-3-ol and 20 ml of N-methylpyrrolidone was maintained at 165° C. for 5 hours to effect a rearrangement of the starting compound. 5 ml of the mixture thus obtained, i.e., a mixture [(I-2):(I-1)= 82.8/17.2] of 6,9,10-trimethyl-3,6,9-undecatrien-2-one [designated (I-2)] and 6,9,10-trimethyl-3,5,9-undecatrien-2-one [designated (I-1)], was mixed with 0.5 weight %, based on said ketone mixture, of iodine and 5 ml of ethanol. The isomerization reaction was thus conducted at the reflux temperature of ethanol with stirring for 2 hours. The ratio of (I-2) ketone to (I-1) ketone in the reaction mixture was 6.3/94.7.

EXAMPLE 44

(1) Production of the α.β,δ.ε-unsaturated ketone

In a three-necked flask of 200 ml capacity, a mixture of 26.2 g of 4-isopropenyl-3,7,11-trimethyldodeca6,10-dien-1-yn-3-ol (purity 84.1%) and 90 ml of N-methylpyrrolidone was maintained at a temperature of 165° C. under nitrogen atmosphere for 4 hours. The reaction mixture was directly distilled in vacuo to recover 15.2 g of a highboiling fraction predominantly consisting of 6,10,14-trimethyl-3,6,9,13-pentadecatetraen-2-one (b.p. 134°-138° C./0.49 mmHg) [designated (I-2)].

(2) Isomerization of the α.β,δ.ε-unsaturated ketone

In a three-necked flask of 20 ml capacity, a mixture of 3.5 g of the above distillate, 8 ml of ethanol and 0.0175 g of iodine was stirred at the reflux temperature of ethanol for 3 hours to effect the isomerization reaction. The reaction mixture was poured into water and extracted with ether. The ethereal layer was dried over anhydrous magnesium sulfate and distilled to remove the ether. The residue was distilled under reduced pressure to recover 2.5 g of a fraction boiling at 131°-139° C./0.11-0.13 mmHg. This distillate was found to be substantially consisting of 6,10,14-trimethyl-3,5,9,13-pentadecatetraen-2-one [designated (I-1)].

(I-2) Infrared absorption spectrum (cm$^{-1}$): 2960, 2920, 2850, 1715, 1680, 1620, 1440, 1375, 1355, 1155, 965

(I-1) Infrared absorption spectrum (cm$^{-1}$): 2960, 2910, 2820, 1665, 1625, 1585, 1440, 1360, 1250, 1155, 1170, 970, 885

EXAMPLE 45

Under nitrogen atmosphere, a mixture of 48 g of 4-isopropenyl-3,7-dimethyl-1-octyn-6-en-3-ol, 160 ml of N-methylpyrrolidone and 0.24 g of iodine was heated to 165° C. with stirring for 4 hours, whereby both the rearrangement and isomerization reactions were conducted. The reaction mixture was directly distilled to recover, as a high-boiling fraction, 31.1 g of a mixture of 6,10-dimethyl-3,6,9-undecatrien-2-one (I-2) and 6,10-dimethyl-3,5,9-undecatrien-2-one (I-1). The ratio of (I-2) to (I-1) was 53:94.7.

What is claimed is:

1. A process for preparing unsaturated ketones which comprises the step of subjecting a substituted propargyl alcohol of formula (III)

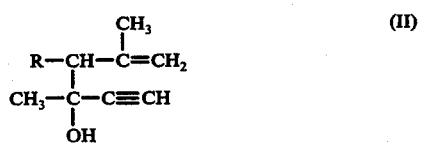

wherein R represents a

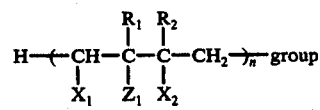

group wherein one of the substituents $X_1$ and $X_2$ is hydrogen and the other and $Z_1$ together form a bond or both $X_1$ and $X_2$ are hydrogen and $Z_1$ represents hydrogen, hydroxyl or lower alkoxy having 1 to 4 carbon atoms, $R_1$ represents a hydrogen or lower alkyl having 1 to 5 carbon atoms, $R_2$ represents hydrogen or lower alkyl and $n$ represents 1 or 2 whereby if $n$ is 2, the substituents $X_1$, $X_2$, $Z_1$, $R_1$ and $R_2$ within the 2 units are alike or different from each other, to a thermal treatment at a temperature of 100° to 400° C. sufficient to rearrange its structure to obtain a rearranged ketone product containing structurally isomeric unsaturated ketones of formula (I)

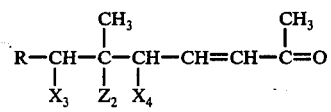  (I)

wherein one of the substituents $X_3$ and $X_4$ is hydrogen and the other and $Z_2$ together form a bond and R is as defined above.

2. The process as defined in claim 1, wherein said heating is performed in a liquid phase and at a temperature in the range of 100° to 250° C.

3. The process as defined in claim 2, wherein said heating is performed in the presence of a liquid polar organic compound selected from the group consisting of compounds containing a sulfoxide group $>S\rightarrow O$, an amido group

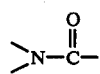

or a phosphoryl group

in its molecule.

4. The process as defined in claim 3, wherein said polar organic compound is selected from the group of dimethylsulfoxide, diethylsulfoxide and tetramethylenesulfoxide.

5. The process as defined in claim 3, wherein said polar organic compound is selected from the group of dimethylformamide, dimethylacetamide, diethylformamide, diethylacetamide, pyrrolidone, N-methylpyrrolidone, N-ethylpyrrolidone and ε-caprolactam.

6. The process as defined in claim 3, wherein said polar organic compound is selected from the group of hexamethylphosphoramide, hexaethylphosphoramide, trimethyl phosphate and triethyl phosphate.

7. The process as defined in claim 3, wherein the heating is performed under an inert gaseous atmosphere.

8. The process as defined in claim 1, wherein said heating is effected in a gaseous phase at a temperature in the range of 250° and 400° C.

9. The process as defined in claim 8, wherein said heating is effected under inert gaseous atmosphere.

10. The process as defined in claim 1, wherein said unsaturated ketone of formula I is an α.β,γ.δ-unsaturated ketone having formula (I-1)

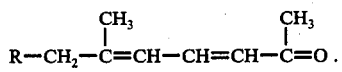  (I-1)

11. The process as defined in claim 1, wherein said unsaturated ketone of formula I is an α.β,δ.ε-unsaturated ketone of the following general formula (I-2)

$$R-CH=\overset{CH_3}{\underset{|}{C}}-CH_2-CH=CH-\overset{CH_3}{\underset{|}{C}}=O .\quad\text{(I-2)}$$

12. The process as defined in claim 1, wherein a substituted propargyl alcohol of the general formula (II-a)

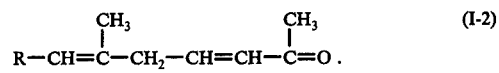  (II-a)

wherein one of the substituents $X_1$ and $X_2$ is hydrogen and the other and $Z_1$ together form a bond and $R_2$ represents hydrogen or methyl is subjected to a thermal treatment sufficient to obtain a rearranged ketone product containing unsaturated ketones of formula (I-a)

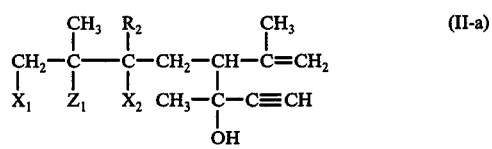  (I-a)

wherein $X_1$, $X_2$, and $R_2$ are as defined in formula (II-a) and $X_3$, $X_4$ and $Z_2$ are as defined in formula I.

13. The process as defined in claim 1, wherein a substituted propargyl alcohol of the general formula (II-b)

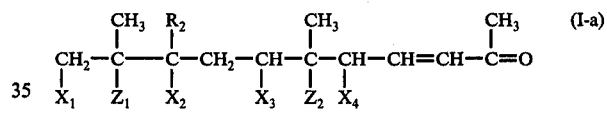  (II-b)

wherein one of the substituents $X_1$ and $X_2$ is hydrogen and the other and $Z_1$ together form a bond whereby $X_1$, $X_2$ and $Z_1$ in the 2 units are alike or different from each other, is subjected to a thermal treatment sufficient to obtain a rearranged ketone product containing unsaturated ketones of formula (I-b)

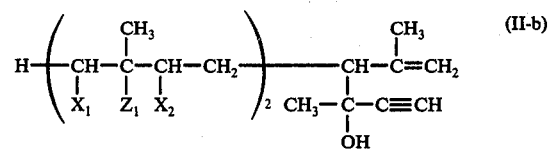  (I-b)

wherein $X_1$, $X_2$ and $Z_1$ are as defined for formula (II-b) and $X_3$, $X_4$ and $Z_2$ are as defined in formula I.

14. The process as defined in claim 1, which further comprises the step of treating said rearranged ketone product with an isomerization catalyst selected from the group consisting of rhodium chloride hydrates, ammonium iodide, hydrogen iodide salts of amines, and iodine at a temperature of 50° C. to 200° C. sufficient to isomerize an α.β,δ.ε-unsaturated ketone of formula (I-2)

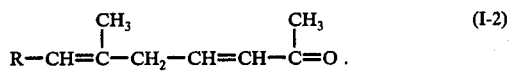

into an α.β,γ.δ-unsaturated ketone of formula (I-1)

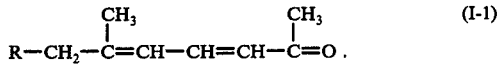

wherein R is as defined in formula II.

15. The process as defined in claim 14, wherein said isomerization step is effected subsequent to the rearrangement reaction.

16. The process as defined in claim 14, wherein said isomerization step is effected simultaneously with the rearrangement step.

17. The process as defined in claim 16, wherein said rearrangement step comprises heating a substituted propargyl alcohol of formula (II) to a temperature of 100° to 250° C. in a liquid phase in the presence of a liquid polar organic compound which is selected from the group of compounds containing an amido group

or a phosphoryl group

in its molecule and in the presence of an isomerization catalyst.

18. The process as defined in claim 17, wherein a substituted propargyl alcohol of the general formula (II-a)

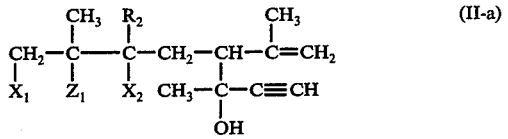

wherein one of the substituents $X_1$ and $X_2$ is hydrogen and the other and $Z_1$ together form a bond and $R_2$ represents hydrogen or methyl
is heated in order to obtain a rearranged product comprising an unsaturated ketone of formula (I-1-a)

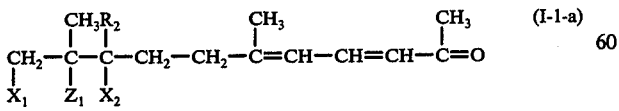

wherein $X_1$, $X_2$ and $R_2$ are as defined in formula (II-a) as a major component.

19. The process as defined in claim 17, wherein a substituted propargyl alcohol of the general formula (II-b)

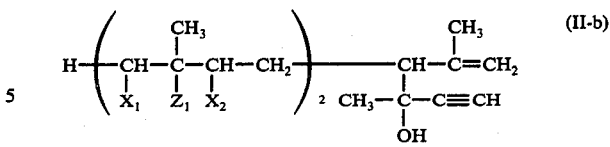

wherein one of the substituents $X_1$ and $X_2$ is hydrogen and the other and $Z_1$ together form a bond whereby $X_1$, $X_2$ and $Z_1$ in the 2 units are alike or different from each other
is heated in order to obtain a rearranged product comprising an unsaturated ketone of formula (I-1-b)

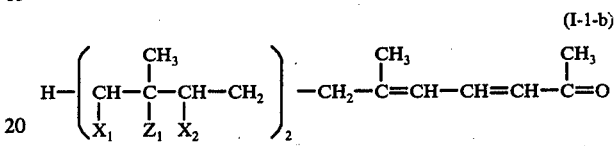

wherein $X_1$, $X_2$ and $Z_1$ are as defined for formula (II-b) as a major component.

20. The process as defined in claim 1, which further comprises the steps of
(a) reacting at least one compound of the group of 4-methyl-3-pentene-2-one and 4-methyl-4-pentene-2-one with a compound of the formula R-halo., wherein R is as defined in formula II and halo represents a halogen atom in the presence of an alkaline condensing agent and a catalyst selected from the group consisting of tetrabutylammonium chloride, trimethylbenzylammonium chloride, trimethyllaurylammonium chloride, trimethylcetylammonium chloride, trimethylstearylammonium chloride, trimethylstearylammonium bromide, dimethyldicyclohexylphosphonium chloride, methyltricyclohexylphosphonium chloride, ethyltricyclohexylphosphonium chloride, and ethyltricyclohexylphosphonium bromide, to obtain a reaction product comprising at least one compound of the group of ketones of formula (III) and formula (IV)

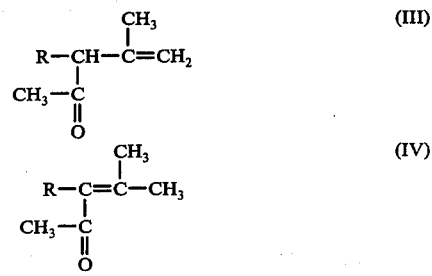

wherein R is as defined in formula II
(b) ethynylating said first reaction product by reacting the same with acetylene in the presence of a strongly basic alkali metal compound and in the presence of at least one solvent from the group of polar organic solvent and liquid ammonia and
(c) recovering a substituted propargyl alcohol of formula II from the ethynylation product.

21. The process as defined in claim 20, wherein said ethynylation step comprises separating the ketone of formula III from other byproducts within said reaction product prior to the ethynylation of said ketone of formula III.

22. The process as defined in claim 20, wherein said ethynylation step (b) comprises subjecting said reaction product to isomerization conditions sufficient to isomerize a ketone of formula IV into a ketone of formula III.

23. The process as defined in claim 22, wherein said isomerization is effected prior to the reaction with acetylene.

24. The process as defined in claim 20, wherein the reaction with acetylene is effected under an elevated acetylene pressure sufficient to effect an isomerization of a ketone of formula IV into a ketone of formula III.

25. The process as defined in claim 24, wherein the elevated acetylene pressure corresponds to a partial pressure of from 1 kg/cm² gauge to 15 kg/cm² at 0° C.

26. A process for preparing a compound of formula (V)

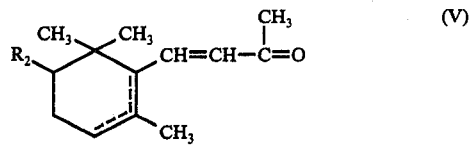

wherein $R_2$ is hydrogen or methyl
comprising the steps of
subjecting a substituted propargyl alcohol of formula (II-a')

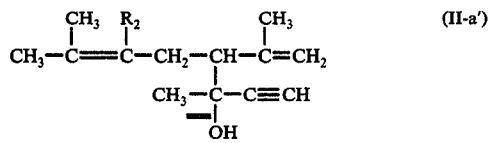

to a thermal treatment as defined in claim 1 and cyclizing in the presence of phosphoric acid as an acid catalyst the resulting ketone of formula (I-a')

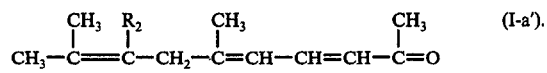

27. The process as defined in claim 26, wherein the compound of formula V is an ionone.

28. The process as defined in claim 26, wherein the compound of formula V is an irone.

* * * * *